(12) United States Patent
Toksoz et al.

(10) Patent No.: US 9,956,362 B2
(45) Date of Patent: May 1, 2018

(54) TRIGGER MECHANISM FOR INHALER DEVICE

(71) Applicant: Arven Ilac Sanayi Ve Ticaret A.S., Istanbul (TR)

(72) Inventors: Zafer Toksoz, Istanbul (TR); Umit Cifter, Istanbul (TR); Ali Turkyilmaz, Istanbul (TR); Onur Mutlu, Istanbul (TR)

(73) Assignee: Arven Ilac Saniyi ve Ticaret A.S., Istanbul (TR)

(*) Notice: Subject to any disclaimer, the term of this patent is extended or adjusted under 35 U.S.C. 154(b) by 608 days.

(21) Appl. No.: 14/403,352

(22) PCT Filed: May 16, 2013

(86) PCT No.: PCT/TR2013/000140
§ 371 (c)(1),
(2) Date: Nov. 24, 2014

(87) PCT Pub. No.: WO2013/176636
PCT Pub. Date: Nov. 28, 2013

(65) Prior Publication Data
US 2015/0136128 A1    May 21, 2015

(30) Foreign Application Priority Data

| May 25, 2012 | (TR) | 2012/06167 |
| Feb. 8, 2013 | (TR) | 2013/01562 |
| Feb. 15, 2013 | (TR) | 2013/01847 |

(51) Int. Cl.
*A61M 15/00* (2006.01)

(52) U.S. Cl.
CPC .... *A61M 15/0051* (2014.02); *A61M 15/0021* (2014.02); *A61M 15/0043* (2014.02);
(Continued)

(58) Field of Classification Search
CPC .......... A61M 15/0021; A61M 15/0026; A61M 15/0043; A61M 15/0051; A61M 15/0055; A61M 2202/064; A61M 2205/70
See application file for complete search history.

(56) References Cited

U.S. PATENT DOCUMENTS

| 5,921,237 A | 7/1999 | Eisele et al. |
| 2002/0032409 A1 | 3/2002 | Ritsche |

(Continued)

FOREIGN PATENT DOCUMENTS

| EP | 2239002 A1 | 10/2010 |
| WO | WO-2006/123110 A1 | 11/2006 |

(Continued)

OTHER PUBLICATIONS

International Preliminary Report on Patentability for International Application No. PCT/TR2013/000140, dated Nov. 25, 2014 (6 pages).

(Continued)

*Primary Examiner* — Bradley Philips
(74) *Attorney, Agent, or Firm* — Liang, Frank & King, LLP

(57) ABSTRACT

The present invention relates to a dry powder inhaler device comprising a body having a guide surface formed on an inner surface thereof, a trigger having a socket with a shape complementing the guide surface, and a spring, characterized by comprising at least one retaining element (8) positioned on the inner surface (1) of the body diagonally across the spring (6) to enable the trigger (5) to perform a stable axial displacement and a mechanism check or quality control to be made as one of the parts of the device (7) body is not closed or assembled yet.

20 Claims, 11 Drawing Sheets

(52) U.S. Cl.
    CPC ..... *A61M 15/0055* (2014.02); *A61M 15/0026* (2014.02); *A61M 2202/064* (2013.01); *A61M 2205/70* (2013.01)

(56) References Cited

U.S. PATENT DOCUMENTS

| | | |
|---|---|---|
| 2011/0232637 A1 | 9/2011 | Kaemper et al. |
| 2015/0096563 A1 | 4/2015 | Toksoz et al. |

FOREIGN PATENT DOCUMENTS

| | | |
|---|---|---|
| WO | WO-2007/012871 A1 | 2/2007 |
| WO | WO-2007/068900 A2 | 6/2007 |
| WO | WO-2010/114504 A1 | 10/2010 |
| WO | WO-2010/114505 A1 | 10/2010 |
| WO | WO-2010/114506 A1 | 10/2010 |
| WO | WO-2011/129788 A1 | 10/2011 |
| WO | WO-2013/176640 A1 | 11/2013 |

OTHER PUBLICATIONS

International Preliminary Report on Patentability for International Application No. PCT/TR2013/000168, dated Nov. 25, 2014 (7 pages).

International Search Report and Written Opinion for International Application No. PCT/TR2013/000140, dated Oct. 14, 2013 (9 pages).

International Search Report and Written Opinion for International Application No. PCT/TR2013/000168, dated Oct. 1, 2013 (10 pages).

Search Report and Written Opinion for Turkish Patent Application No. 201301847, completed Jan. 9, 2014 (8 pages).

TRIGGER MECHANISM FOR INHALER DEVICE

FIELD OF INVENTION

The present invention relates to a device for administering dry powder inhalation drugs.

The present invention particularly relates to improvements made in the trigger part of dry powder inhaler devices.

PRIOR ART

Diseases such as asthma, bronchitis, and COLD (Chronic Obstructive Lung Disease) substantially decrease the quality of human life, despite the developments which have been made in the diagnosis and therapy thereof in the recent years. It has been proposed to administer medicaments via inhalers for optimizing the treatment of such diseases. The inhaler route of treatment is the most preferred one and it is expected to remain so, as the first option, in the future. The most important advantage of using medicaments via inhalation is based on providing a more efficient therapy by making use of lower amounts of medicaments, delivering higher concentrations of medicaments to the airways, and particularly decreasing the systemic side effects of the medicaments. The most important causes of the lack of a satisfactory control of patients albeit the presence of quite efficient treatments against respiratory tract diseases are stated to be as the noncompliance, arising from the inefficient use of inhalers and from inadequate compliance to the physician-recommended treatments.

There have been developed various inhalation devices for administering inhalation medicaments nowadays. These devices are basically classified into two groups, i.e. metered dose inhalers and dry powder inhalers. These type of devices are structurally provided with basic units such as an actuator, trigger, housing, mouthpiece, lid, lock, etc. Additionally, powder inhalation medicaments are kept in carriers such as blisters, capsules, etc. Blisters are composed of two basic parts, a main layer provided with cavities carrying the medicament, and a strippable protective layer.

A user inhales the respective medicament by means of a mouthpiece provided at the respective dry powder inhaler device with the aid of his/her breath, so that the powder drug is delivered to the lungs, the target organs. The drug, which is released with the opening of a blister or with the explosion of a capsule in blister- or capsule-inhalers is guided to the mouthpiece and is kept in a site which is in connection with the mouthpiece. The mouthpiece, in turn, is designed with a size and length to comply with the anatomy of the human mouth. Thus, both the administration of the drug is facilitated and hygiene compliance is ensured. Inhaling air into the lungs is an active action. With the contraction of inspiration muscles, the front and rear diameters of the chest cage are expanded and it is elongated from top to down. According to the law of Boyle-Mariotte, when the volume of a gas increases, its pressure drops down. According to that law, since the pressure of air in the lungs will be lower in expanding lungs than that of atmospheric air, atmospheric air will fill the lungs. Air flow resulting from atmospheric air inhaled into the lungs allows the administration of a powder drug without requiring any other force. The powder drug in the device is delivered into the body via air flow.

To the mechanism providing the motion of blisters in inhaler devices which comprise multiple blisters are exerted a force by means of a trigger or a lever and the mechanism is actuated accordingly. However, various problems are encountered in using the trigger mechanism. Some of these are related to the levers actuating the mechanism. Such levers bring about some drawbacks such as difficulty in use and an extra movable volume requirement on the exterior of the inhaler body. Some sliding types do also have some problems. In the applications WO2010114506 and WO2010114505, for instance, the linear motion performed by a trigger is converted into a circular motion by means of a gear. This trigger is slid into a slot provided in the device body to provide an axial motion, such that the force resulting from this motion is transmitted to a blister advancement mechanism in the device by means of a gear with which the trigger is in engagement. The displacement of the trigger is guided by means of mutually-compatible surfaces disposed on the body of the trigger and in the interior of the device body, and the forward and rearward sliding extent of the trigger is determined by means of these surfaces. This type of guiding provided from the middle part of the trigger body, however, makes the trigger loose or slacking as it is displaced and dislocates it from the slot it is slid in. Whilst forming a track along the lower and upper edges of the trigger may provide a solution, this prolongs the assembly time of the device and leads to some difficulties.

Another main problem is encountered in the assembly step of the device while the mechanism is tested before one of the two body parts is closed. The mechanism is placed into one of these parts, and the other part is closed on the former part to build the body. The device should be checked for proper operation before the upper pars is mounted. The inner mechanism of the device comprises interconnected gears and a spring to wind up the mechanism of the device. Accordingly, the interior of the device comprises surfaces which are under strain to ensure the assembly and operation of the device. It is not possible to squeeze the trigger and to check the device unless these two parts are assembled. If the device is subjected to quality control before both parts are assembled, the entire mechanism in the device comes apart and resultantly the quality check can not be performed. Here, it is important to keep the mechanism in the body as a whole in an assembled and operable state in which it can be checked visually.

In result, there is a novelty required in the trigger mechanism of inhaler devices, providing high-accuracy operability, as well as advantages in terms of assembly, quality control and use.

OBJECTS AND BRIEF DESCRIPTION OF INVENTION

The present invention relates to a dry powder inhaler device having a novel trigger mechanism, eliminating all aforesaid problems and bringing additional advantages to the relevant prior art.

Accordingly, the main object of the present invention is to provide an inhaler device comprising a trigger embodiment which can be slid and guided in a stable manner during use.

Another object of the present invention is to provide an inhaler device comprising a trigger embodiment by which the device can be subjected to quality control without the mechanism placed in one of the parts of the two-part body coming apart.

A further object of the present invention is to provide an inhaler device comprising a trigger embodiment which provides an easy assembly.

In order to achieve all objects described above and to emerge in the following detailed description, a dry powder inhaler device has been developed, which comprises a body having a guide surface formed on an inner surface thereof, a trigger having a socket with a shape complementing the guide surface, and a spring.

In a preferred embodiment according to the present invention, the novelty is characterized by comprising at least one retaining element positioned on the inner surface of the body diagonally across the spring, in order to enable the trigger to perform a stable axial displacement and a mechanism check to be made as one of the parts of the device body is not assembled yet.

In a preferred embodiment of the present invention, the retaining element comprises at least one fastening tab.

In a preferred embodiment of the present invention, the retaining element comprises at least one channel.

In a preferred embodiment of the present invention, the retaining element is positioned diagonally across the spring.

Structural and characteristic features, and all advantages of the present invention shall be made clear by means of the accompanying figures described here below and a detailed description written by making references to said figures; therefore, the present invention must be evaluated by taking into consideration these figures and the detailed description as well.

REFERENCE NUMBERS IN FIGURES

Figure 1:
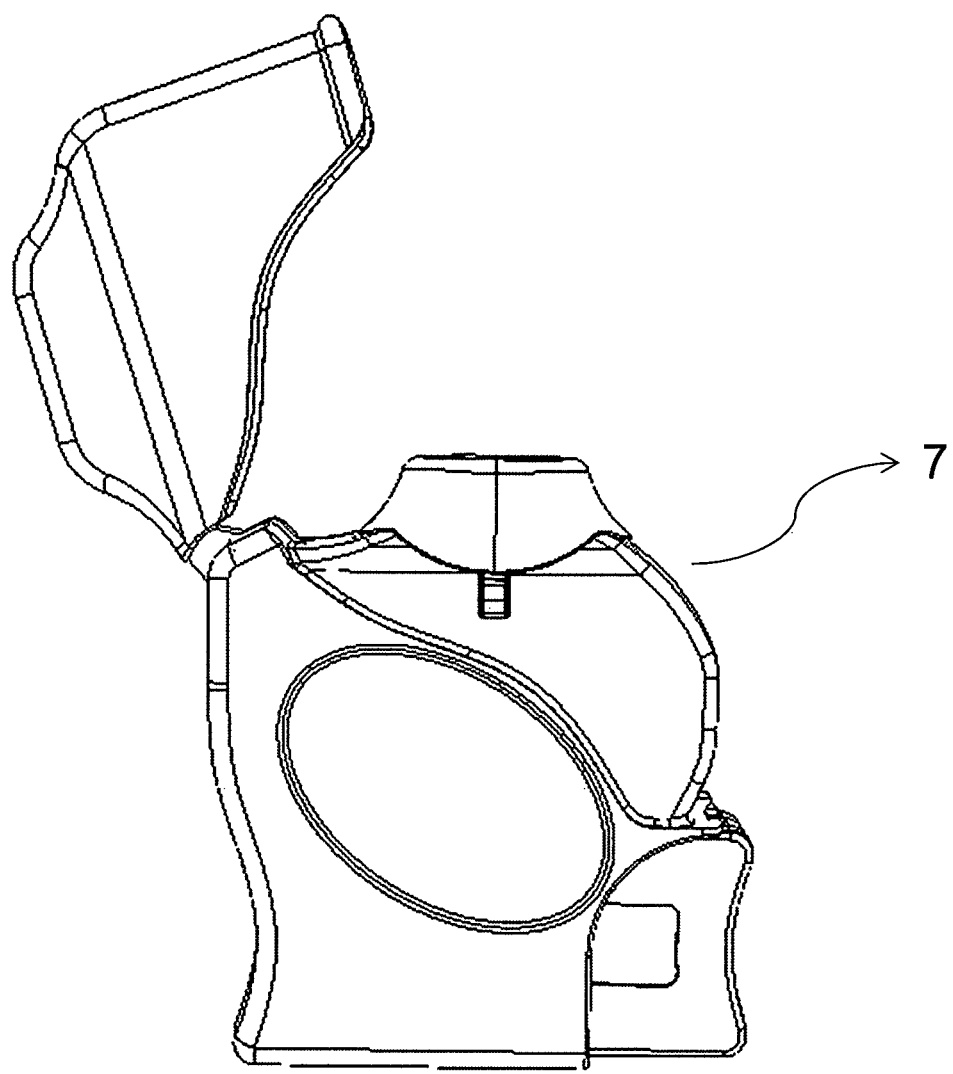
FIG. 1 is a schematic view of a representative embodiment of the inhaler device according to the present invention.

1. Inner surface of the body
2. Guide surface
3. Body
4. Trigger socket
5. Trigger
6. Spring
7. Inhaler device
8. Retaining element
9. Fastening tab
10. Channel

DETAILED DESCRIPTION OF INVENTION

In the following detailed description, an inhaler device (7) according to the present invention shall be described illustratively by making references to the accompanying figures, only to make it clear without imposing any restrictions thereon.

Figure 2:
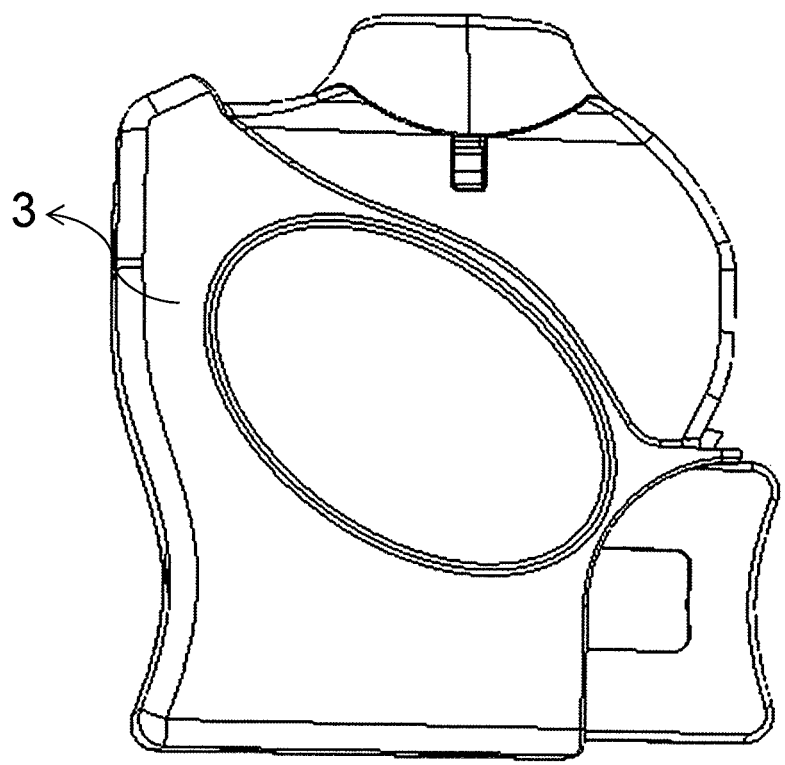
FIG. 2 is a schematic view of a representative embodiment of the body of the inhaler device according to the present invention.
Figure 3:
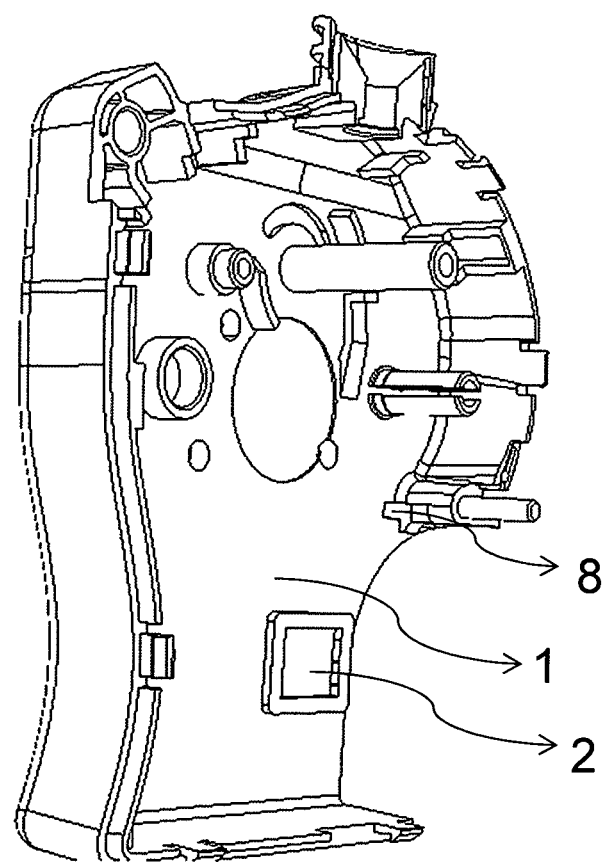
FIG. 3 is a schematic view of a representative embodiment of one of the parts of the device body according to the present invention.
Figure 4:
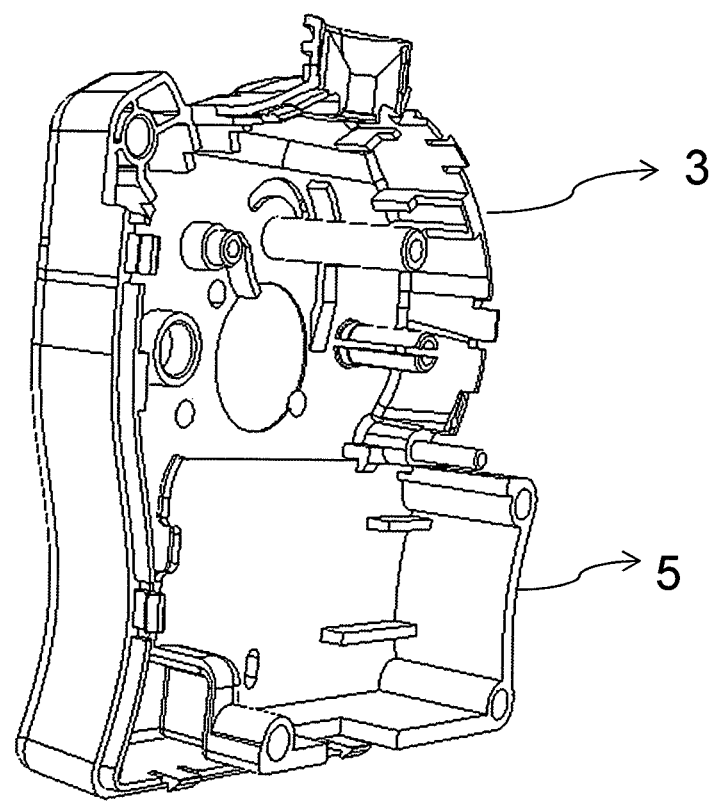
FIG. 4 is a schematic view of a representative embodiment of one part of the device body and the trigger according to the present invention.
Figure 5:
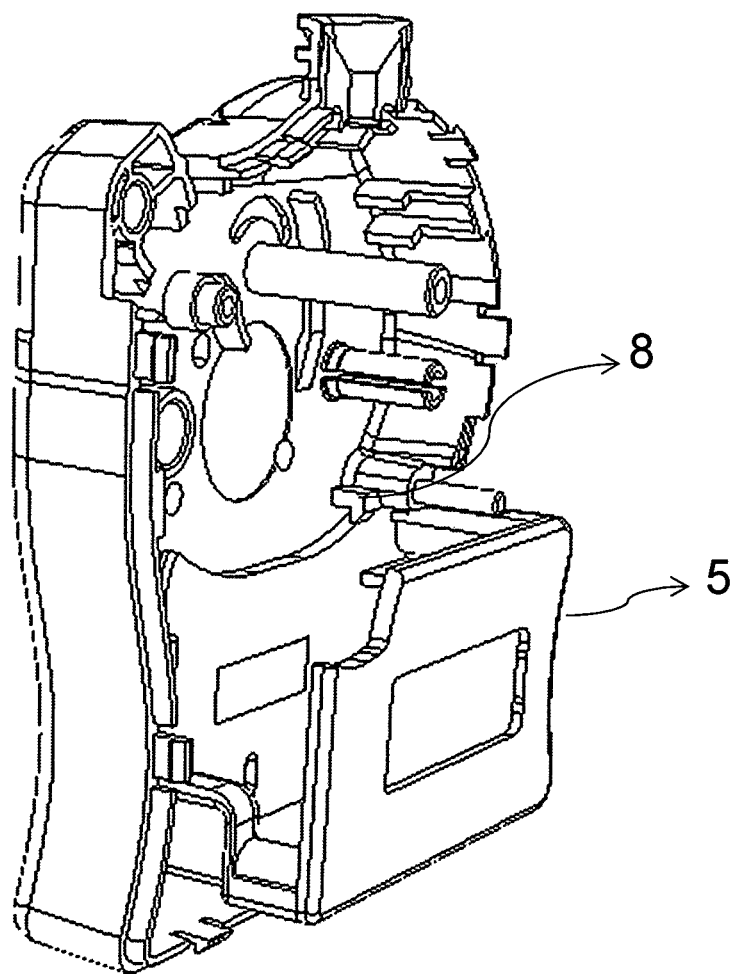
FIG. 5 is a schematic view of a representative embodiment of one part of the device body and the trigger according to the present invention.
Figure 6:
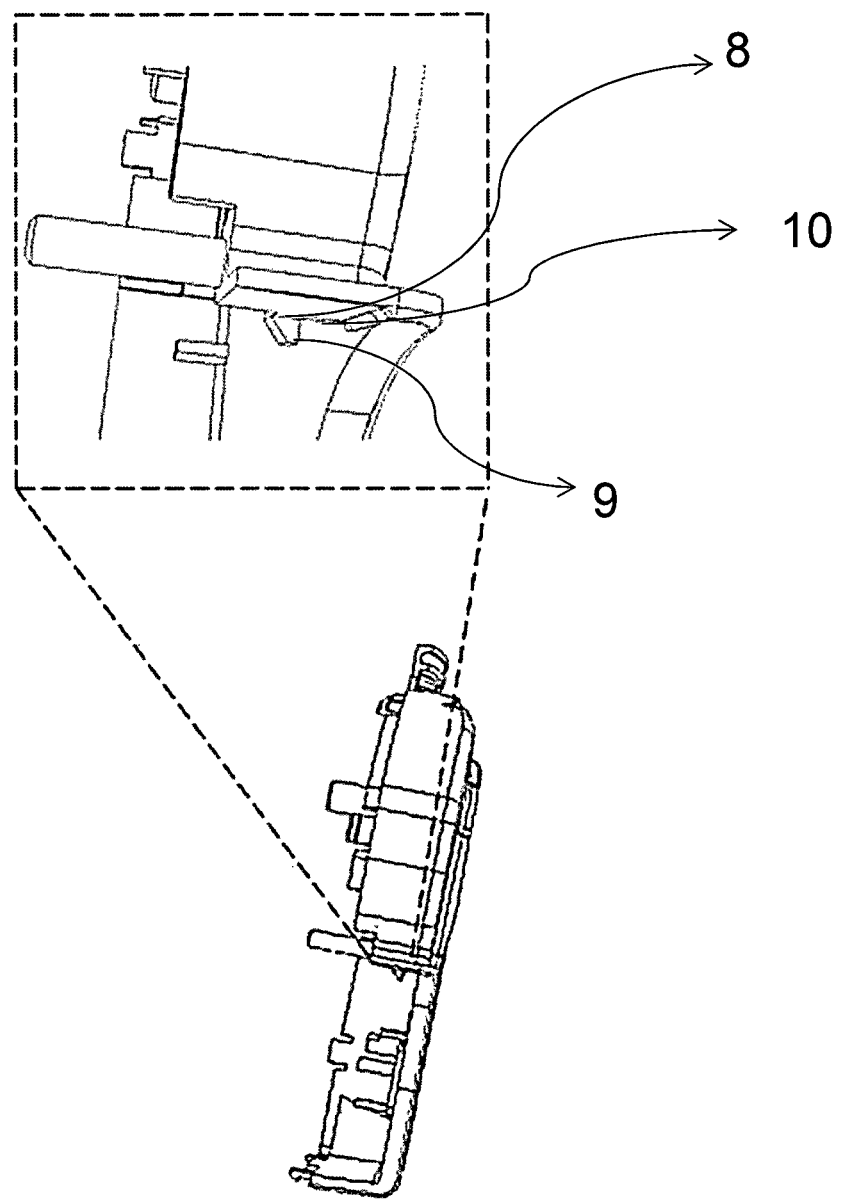
FIG. 6 is a schematic view of a representative embodiment of one part of the device body and a retaining element according to the present invention.
Figure 7:
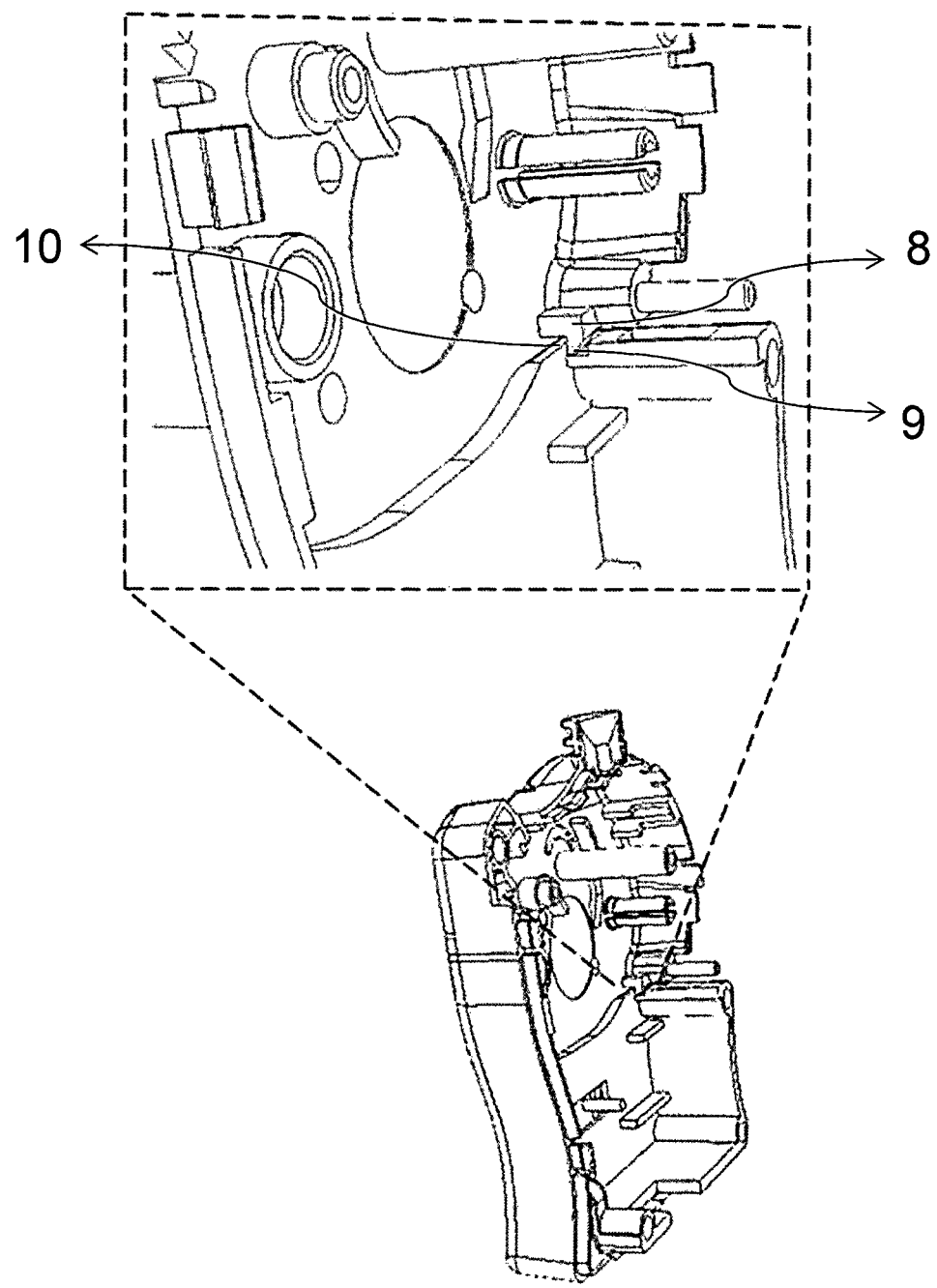
FIG. 7 is a schematic view of a representative embodiment of one part of the device body and the retaining element according to the present invention.
Figure 8:
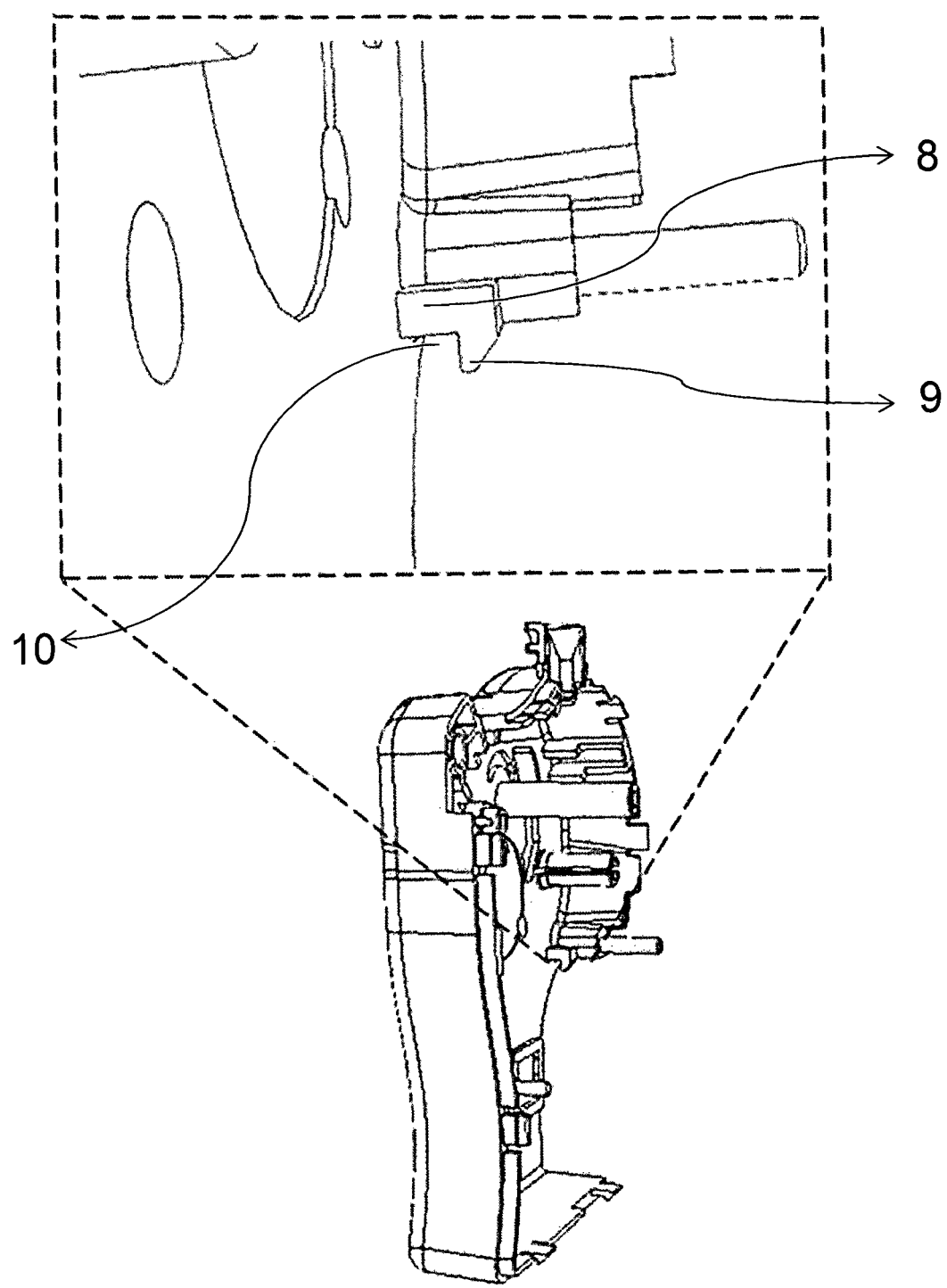
FIG. 8 is a schematic view of a representative embodiment of one part of the device body and the retaining element according to the present invention.
Figure 9:
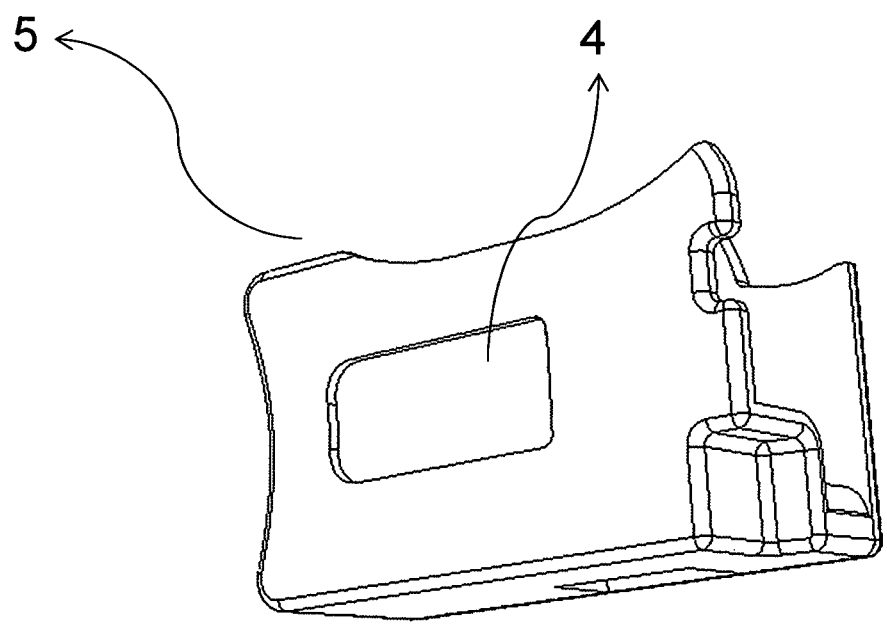
FIG. 9 is a schematic view of a representative embodiment of the trigger of the device according to the present invention.
Figure 10:
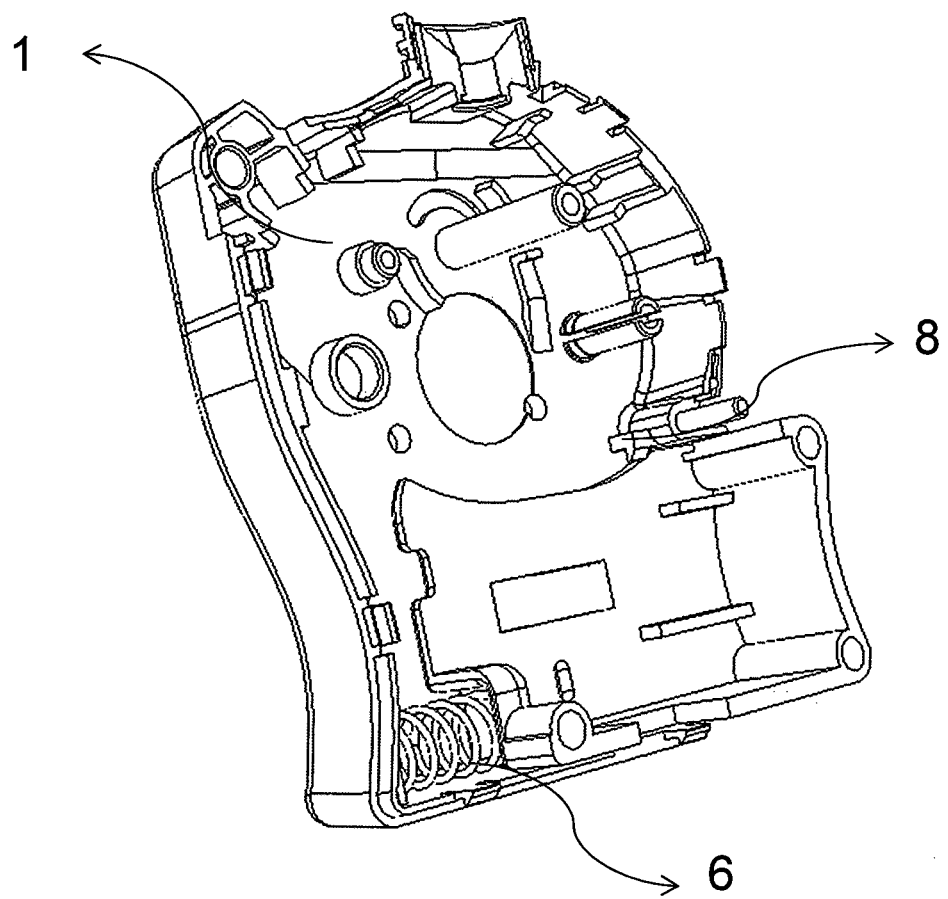
FIG. 10 is a schematic view of a representative embodiment of one part of the device body and a spring according to the present invention.
Figure 11:
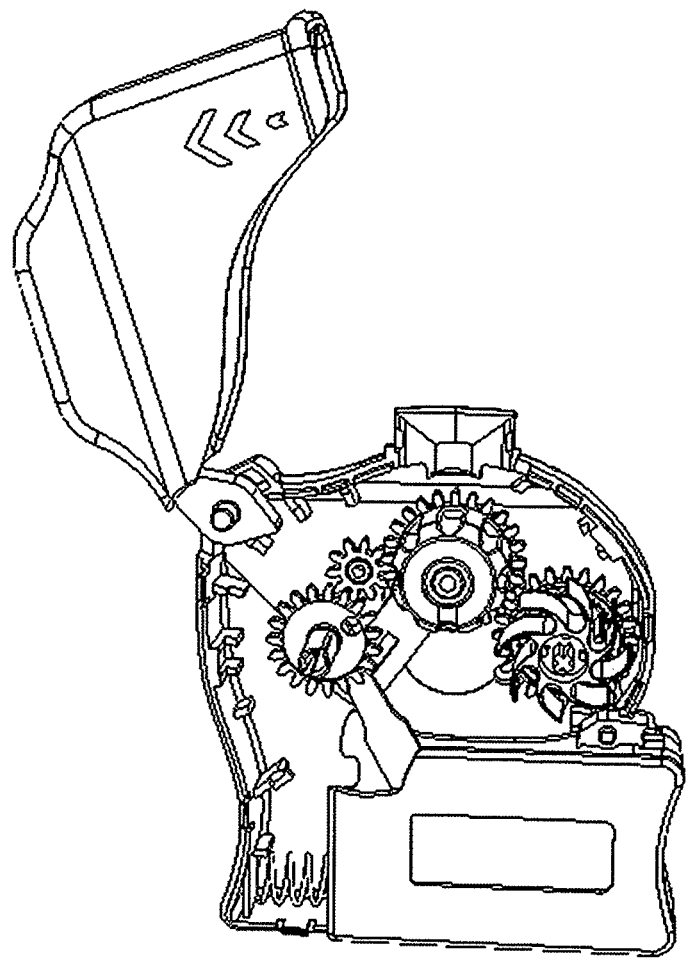
FIG. 11 is a schematic view of a representative embodiment of the inhaler device according to the present invention.

The device (7) according to the present invention of which representative embodiments are shown in FIGS. 1, 2, and 11, has a body (3) comprising an advancement mechanism for a blister with a plurality of cavities. A mouthpiece, which is formed as an extension of the body is provided just on the top of the body. A removable external mouthpiece is provided as well, which envelopes the former mouthpiece and is closed thereon. A gear set of the blister advancement mechanism is disposed in the interior of the body (3) to provide the operation of the inhaler device (7). Along some intermediary channels of this gear set is provided a strip blister having cavities filled with a powder drug.

The device according to the present invention of which representative embodiments are shown in FIGS. 1, 2, 4, 5, 7, 8, 9, and 10, comprises a trigger (5) disposed at the beginning of the blister advancement mechanism and slid into a lower side part of the body (3). Said trigger (5) is capable to be axially displaced within a gap defined by a guide surface (2) provided on the interior of the body (1) and a socket (4) provided on the trigger (5). A surface provided on the exterior of the trigger (5) to which a user exerts force to push in the trigger (5) has an inwardly curved structure to provide ease of use. A spring (6) is disposed between the trigger (5) and the inner surface (1) of the body, the spring being structured to become compressed (i.e. loaded) when the trigger (5) is pushed into the body (3). A retaining element (8) according to the present invention is disposed on the inner surface of the body, diagonally across the spring. A fastening tab (9) is provided on the tip of the retaining element (8). A channel is formed between the retaining element and the inner surface to receive an edge of the trigger (5). The trigger is placed in this channel to slide and displace freely.

The trigger is slid into the device body and locked at a final point it reaches. The blister advancement mechanism is actuated with this sliding action, such that a powder drug is made available for use when a blister is opened. As a result of the sliding action, the trigger (5) becomes locked when it is depressed by virtue of a lock system disposed in the device. The spring (6) becomes compressed and loaded between the trigger and the inner surface of the body. And when the lid is closed, the trigger is released from the lock, is slid backward under the effect of the loaded spring, and is then reloaded and restored for the next use. The mechanism should be tested for proper operation visually before the parts are assembled together. In the assembly step, the mechanism is placed to one of the body parts, and then the other part is closed onto the former part. However, when the mechanism is tested before the body parts are entirely assembled, the components of the mechanism are released from the grooves and the pins and come apart. The present invention was made to prevent this. The retaining element makes it possible to position the trigger in front of the mechanism just like a barrier which prevents the components from coming apart. According to this structure, however, the trigger is not completely fixed, but is free to be slid back and forth. This, in turn, is provided by means of the fastening tab (9) on the retaining element and the channel (10).

Thus, the retaining element (8) is positioned on the inner surface (1) of the body diagonally across the spring (6) to enable the trigger (5) to perform a stable axial displacement and a mechanism check to be made as one of the parts of the device body (7) is not mounted yet. Additionally, the size of the retaining element is quite low, and it is extremely easy to mount and dismount the trigger to/from the channel. The trigger displaced axially in the channel can be moved back and forth stably without any slackness. The spring used in the mechanism on the lower corner of the trigger exerts a force to push the trigger up- and outward. The retaining element counterbalances this thrust from the site it is placed.

In consequence, an extremely-accurate and safely-operable inhaler device is obtained with the embodiment disclosed above.

The design of the parts used may be varied in alternative embodiments according to the type of the device being produced. In result, the protection scope of the present invention is set forth in the accompanying claims and cannot be restricted to the illustrative disclosures given above, under the detailed description. It is obvious that a person skilled in the relevant art can produce similar embodiments under the light of the foregoing disclosures, without departing from the main principles of the present invention.

The invention claimed is:

1. A dry powder inhaler device comprising a body having a guide surface formed on an inner surface of the body, a trigger having a socket with a shape complementing the guide surface, a spring, at least one retaining element positioned on the inner surface of the body diagonally across from the spring with respect to a longitudinal axis of the body, and at least one channel formed by at least one portion of the inner surface of the body and at least one portion of an external surface of the at least one retaining element to enable the trigger to perform a stable axial displacement.

2. The dry powder inhaler device according to claim 1, wherein the retaining element comprises at least one fastening tab.

3. The dry powder inhaler device according to claim 2, wherein the at least one channel is formed by the at least one portion of the inner surface of the body and the at least one fastening tab.

4. The dry powder inhaler device according to claim 1, wherein at least one portion of an edge of the trigger is disposed in the at least one channel.

5. The dry powder inhaler device according to claim 4, wherein the at least one channel enables the trigger to perform the stable axial displacement by sliding in the at least one channel.

6. The dry powder inhaler device according to claim 5, wherein the spring is compressed as the trigger performs the stable axial displacement.

7. The dry powder inhaler device according to claim 6, wherein the device further comprises a locking system, and the trigger is locked when depressed by the locking system disposed in the device.

8. The dry powder inhaler device according to claim 5, wherein the trigger is locked at a final point the trigger reaches.

9. The dry powder inhaler device according to claim 3, wherein at least one portion of an edge of the trigger is disposed in the at least one channel.

10. The dry powder inhaler device according to claim 9, wherein the at least one channel enables the trigger to perform the stable axial displacement by sliding in the at least one channel.

11. The dry powder inhaler device according to claim 9, wherein the spring is compressed as the trigger performs the stable axial displacement.

12. The dry powder inhaler device according to claim 11, wherein the device further comprises a locking system, and the trigger is locked when depressed by the locking system disposed in the device.

13. The dry powder inhaler device according to claim 12, wherein the trigger is locked at a final point the trigger reaches.

14. The dry powder inhaler device according to claim 2, wherein the at least one fastening tab is provided on a tip of the at least one retaining element.

15. The dry powder inhaler device according to claim 3, wherein the at least one fastening tab is provided on a tip of the at least one retaining element.

16. The dry powder inhaler device according to claim 1, wherein the at least one retaining element comprises a major external surface and a minor external surface, with the major external surface running parallel to a longitudinal axis of the at least one retaining element, and wherein the at least one channel is formed by the at least one portion of the inner surface of the body and at least one portion of the major external surface of the at least one retaining element.

17. The dry powder inhaler device according to claim 3, wherein the at least one retaining element further comprises a major external surface and a minor external surface, with the major external surface running parallel to a longitudinal axis of the at least one retaining element, and wherein the at least one channel is formed by the at least one portion of the inner surface of the body, at least one portion of the major external surface of the at least one retaining element, and the at least one fastening tab.

18. The dry powder inhaler device according to claim 6, wherein the spring is compressed between the trigger and a portion of the inner surface of the body.

19. The dry powder inhaler device according to claim 11, wherein the spring is compressed between the trigger and a portion of the inner surface of the body.

20. The dry powder inhaler device according to claim 3 further comprises other components, wherein the at least one retaining element prevents the other components from coming apart before the inhaler device is completely assembled or completely closed.

* * * * *

UNITED STATES PATENT AND TRADEMARK OFFICE
CERTIFICATE OF CORRECTION

PATENT NO. : 9,956,362 B2
APPLICATION NO. : 14/403352
DATED : May 1, 2018
INVENTOR(S) : Zafer Toksoz, Ali Turkyilmaz and Onur Mutlu Page 1 of 1

It is certified that error appears in the above-identified patent and that said Letters Patent is hereby corrected as shown below:

On the Title Page

Please replace the line pertaining to the assignee name:
"(73) Assignee: Arven Ilac Saniyi ve Ticaret A.S."
With:
--(73) Assignee: Arven Ilac Sanayi ve Ticaret A.S.--

Signed and Sealed this
Seventh Day of August, 2018

Andrei Iancu
*Director of the United States Patent and Trademark Office*